(12) United States Patent
Oosawa

(10) Patent No.: US 8,788,014 B2
(45) Date of Patent: Jul. 22, 2014

(54) MAGNETIC RESONANCE IMAGING APPARATUS, BED DEVICE FOR MAGNETIC RESONANCE IMAGING APPARATUS AND TABLE TOP OF BED DEVICE FOR MAGNETIC RESONANCE IMAGING APPARATUS

(75) Inventor: Takuhiro Oosawa, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 516 days.

(21) Appl. No.: 12/613,169

(22) Filed: Nov. 5, 2009

(65) Prior Publication Data

US 2010/0113913 A1 May 6, 2010

(30) Foreign Application Priority Data

Nov. 6, 2008 (JP) .................................. 2008-285569

(51) Int. Cl.
*A61B 5/055* (2006.01)
(52) U.S. Cl.
USPC .............................................. 600/410; 5/601
(58) Field of Classification Search
USPC ....................................... 5/601; 600/410, 415
See application file for complete search history.

(56) References Cited

U.S. PATENT DOCUMENTS

| 3,663,346 A * | 5/1972 | Schoen .......................... 428/116 |
| 4,956,885 A * | 9/1990 | Alich et al. ....................... 5/601 |
| 5,280,428 A * | 1/1994 | Wu et al. ........................ 600/407 |
| 5,950,627 A * | 9/1999 | Bologovsky et al. .......... 128/869 |
| 2006/0185087 A1* | 8/2006 | Coppens et al. .................. 5/601 |

FOREIGN PATENT DOCUMENTS

| JP | 5-115457 | 5/1993 |
| JP | 05-062208 | 8/1993 |
| JP | 2004-216021 | 8/2004 |
| JP | 2008-000247 | 1/2008 |
| JP | 2008-006200 | 1/2008 |

* cited by examiner

*Primary Examiner* — Parikha Mehta
(74) *Attorney, Agent, or Firm* — Oblon, Spivak, McClelland, Maier & Neustadt, L.L.P.

(57) ABSTRACT

A number of C-FRP molded material sections that are elongated and made from a carbon fiber reinforced plastic are placed parallel to each other. The C-FRP molded material sections are insulated from each other by honeycomb material sections that are made from an insulating and nonmagnetic material. The C-FRP molded material sections and the honeycomb material sections are maintained by a glass fiber layer into a sheet plate shape.

36 Claims, 10 Drawing Sheets

MAGNETIC RESONANCE IMAGING APPARATUS, BED DEVICE FOR MAGNETIC RESONANCE IMAGING APPARATUS AND TABLE TOP OF BED DEVICE FOR MAGNETIC RESONANCE IMAGING APPARATUS

CROSS-REFERENCE TO PRIORITY APPLICATIONS

The present application is based on and claims priority to Japanese Patent Application No. P2008-285569 filed on Nov. 6, 2008, the entire contents of which is hereby incorporated herein by reference.

BACKGROUND OF THE INVENTION

1. Field of the Invention

The present invention relates to magnetic resonance imaging apparatuses, and more particularly to bed devices to feed subjects into imaging spaces and table tops of the bed devices.

2. Description of the Related Art

A table top to feed a subject into an imaging space for example of a MRI apparatus is required to be nonmagnetic and nonconductive to prevent observing a magnetic resonance phenomenon in the subject. Therefore, the table top is conventionally composed of a wood material. Recently, to be craft friendly or for weight saving, it has become common for the table top to be composed of glass fiber reinforced plastic (G-FRP) (see Jpn. Pat. App. KOKAI Publication No. 2008-006200).

However, recently it is necessary for an MRI apparatus to scan a wide range with one search for a screening scan etc. Therefore, a range of movement for the bed device has widened. A wider range of the bed device improves a maximum overhang length from the bed device to the table top. Meanwhile, a magnetic gantry that generates static magnetic control that tends to shorten an axis and consequently the length of a projecting part of the table top in the direction of backward of the magnetic gantry (opposite side of the bed device) has had to be lengthened. Therefore, the table top is being required to support a greater load.

From the above facts, sometimes wood and G-FRP do not provide all the properties currently being required from the bed device. In addition, although G-FRP gives a certain level of strength of the bed device by heightening to a filling fraction of a glass fiber in the G-FRP, the more the filling fraction of the glass fiber in G-FRP is increased, the greater a strain in molding the G-FRP and the heavier the G-FRP.

SUMMARY OF THE INVENTION

In view of such circumstances, an object of the present invention is to provide a table top that is light and easy to mold and with high strength.

BRIEF DESCRIPTION OF THE DRAWINGS

The accompanying drawing, which are incorporated in and constitute a part of the specification, illustrate embodiments of the invention, and together with the general description given above and the detailed description of the embodiments given below, serve to explain the principles of the invention, in which.

DETAILED DESCRIPTION OF PREFERRED EMBODIMENTS

Figure 1:
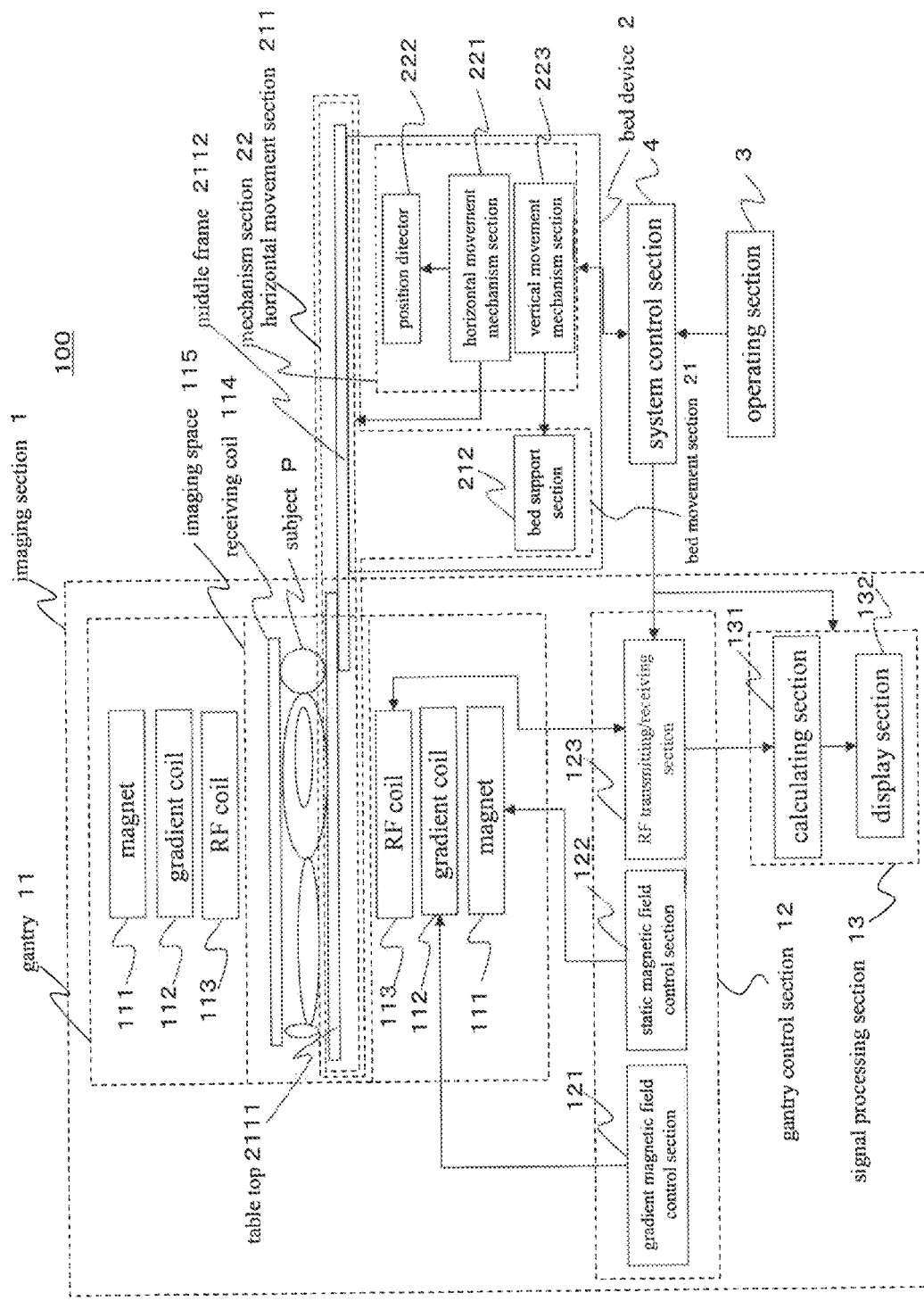
FIG. 1 is a block diagram showing a structure of an MRI apparatus according to an embodiment of the invention.

A magnetic resonance imaging apparatus (an MRI apparatus) according to an embodiment of the invention will now be explained with reference to the figures. At first, units of a MRI apparatus 100 according to this embodiment will be explained. FIG. 1 is a block diagram showing a structure of an MRI apparatus 100 according to this embodiment.

The MRI apparatus 1 includes an imaging section 1, a bed device 2, an operating section 3, and a system control section 4. The imaging section 1 collects a magnetic resonance signal (an MR signal) from a subject P, and performs an arithmetic operation based on the collected MR signal. The bed device 2 sets the subject P at an imaging position of the imaging section 1. The operating section 3 accepts an operation by an operator to control the imaging section 1 and the bed device 2. The system control section 4 controls the imaging section 1 and the bed device 2 based on a signal from the operating section 3.

The imaging section 1 includes a gantry 11, a gantry control section 12, and a signal processing section 13.

The gantry 11 includes a magnet 111, a gradient coil 112, an RF coil 113, and a receiving coil 114. A cylindrical imaging space 115 where the subject P is imaged is formed in the gantry 11. The magnet 111, the gradient coil 112, and the RF coil 113 are arranged such that this imaging space 115 serves as an axis. The magnet 111 generates a static magnetic field in the imaging space 115. For this magnet 111, a superconducting magnet can be utilized, for example. When using a superconducting magnet as the magnet 111, a non-illustrated static power supply is provided. The gradient coil 112 is arranged on an inner circumference of the magnet 111.

The gradient coil 112 generates a gradient magnetic field in the imaging space 115 when a power is supplied from a non-illustrated gradient power supply. The RF coil 113 is arranged on an inner circumference of the gradient coil 112. When a radio frequency signal is supplied from the gantry control section 12, the imaging space 115 is transmitted with a radio frequency pulse to excite a hydrogen atomic nucleus in the subject P by the RF coil 113. The receiving coil 114 is arranged on the bed device 2, and is fed into the imaging space 115 by the bed device 2, at the time of imaging. The receiving coil 114 converts the MR signal emitted as an electromagnetic wave from the subject P into an electric signal state, and outputs the converted MR signal to the gantry control section 12.

The gantry control section 12 includes a gradient magnetic field control section 121, a static magnetic field control section 122, and an RF transmitting/receiving section 123.

The gradient magnetic field control section 121 controls the gradient power supply. The static magnetic field control section 122 controls the static power supply. The RF transmitting/receiving section 123 supplies an RF signal to the RF coil 113. The RF transmitting/receiving section 123 performs reception processing with respect to the MR signals output from the RF coil 113 and the receiving coil 114, and then outputs the processed signals to the signal processing section 13. Further, the RF transmitting/receiving section 123 performs sequence control to carry out generation of a gradient magnetic field, transmission of the RF signal, and reception of the MR signal in accordance with predetermined sequences.

The signal processing section 13 includes a calculating section 131 and a display section 132. The calculating section 131 reconstructs an image from the MR signal supplied from the RF transmitting/receiving section 123. The display section 132 displays the image reconstructed by the calculating section 131. As the display section 132, a CRT (a cathode-ray tube) can be utilized for example.

The bed device 2 includes a bed movement section 21 and a mechanism section 22. The bed movement section 21 includes a horizontal movement section 211 and a bed support section 212. The horizontal movement section 211 includes a table top 2111 and a middle frame 2112. The subject P is mounted on a top surface of the table top 2111. Furthermore, the receiving coil 114 is arranged over the subject P. The middle frame 2112 supports the table top 2111 to be movable in a horizontal direction. The bed support section 212 supports the horizontal movement section 211 to be movable in a vertical direction.

The mechanism section 22 includes a horizontal movement mechanism section 221, a position detector 222, and a vertical movement mechanism section 223. The horizontal movement section 211 horizontally moves the table top 2111. The position detector 222 detects a position of the table top 2111. The vertical movement mechanism section 223 vertically moves the bed support section 212.

The operating section 3 includes a non-illustrated inputting device, for example a keyboard, and a display device. The operating section 3 is used by an operator to input an operation of the bed device 2, e.g. to input a setting for the subject P mounted on the table top 2111 to an appropriate position in the imaging space 115. Moreover, the operating section 3 can be arranged on the gantry 11 to enable an operation near the subject P when moving the subject P. The operating section 3 supplies a signal indicative of contents of an operation input by the operator to the system control section 4.

The system control section 4 includes a CPU, a storage circuit, and other elements. The system control section 4 performs overall control with respect to each section in the MRI apparatus 100 based on an input signal from the operating section 3.

The table top 2111 of the MRI apparatus will now be explained.

Figure 2:
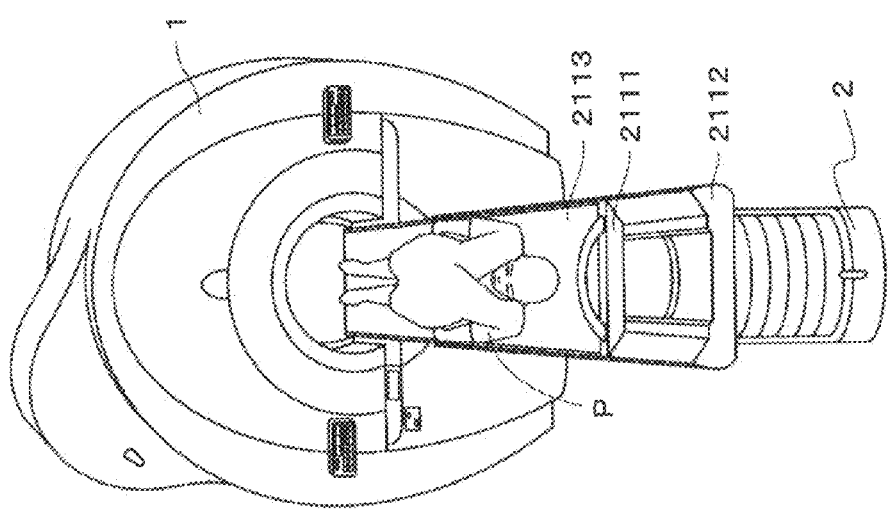
FIG. 2 is a perspective view showing an appearance of an MRI apparatus that has a table top according to the embodiment of FIG. 1.

FIG. 2 is a perspective view showing an appearance of an MRI 100 apparatus that has a table top 2111 according to each embodiment of the invention.

The bed device 2 feeds the subject P that is placed on the table top 2111 into the imaging space 115 by the horizontal movement mechanism section 221 (shown in FIG. 1) moving the table top 2111.

A length of the table top 2111 in the direction the table top 2111 is moved to feed the subject P into the imaging space 115 (the longitudinal direction) is much longer than a length of the table top 2111 at right angles to that moving direction (the cross or width direction).

The following discussion refers to the longitudinal direction of the table top 2111 as the table top longitudinal direction and refers to the direction that lies at right angles to the table top 2111 longitudinal direction as a table top cross or width direction.

Figure 3:
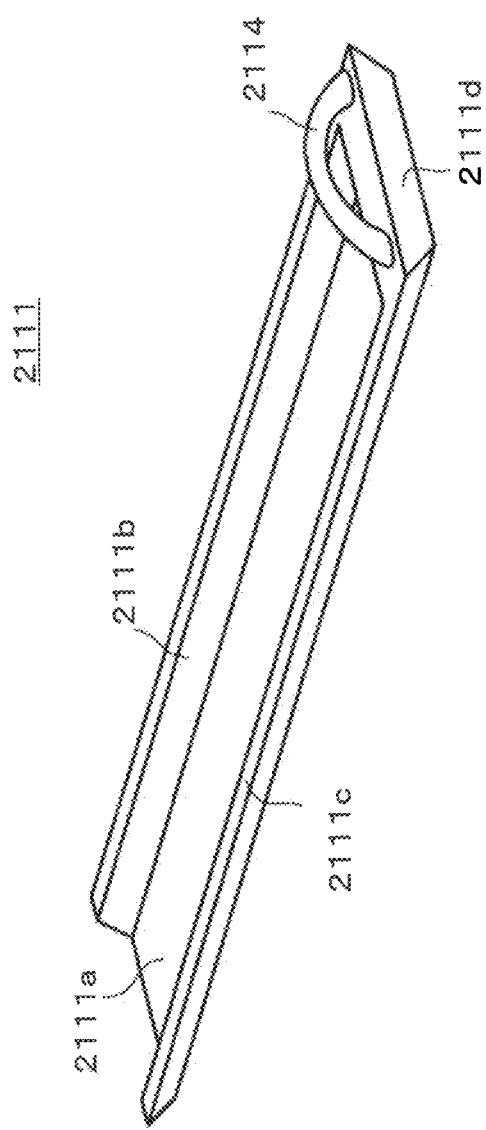
FIG. 3 is a perspective view showing a structure of a part of a table top according to the embodiment of FIG. 1.

FIG. 3 is a perspective view showing a structure of a part of a table top 2111 in FIG. 2.

As shown in FIG. 3, the table top 2111 includes a plate section 2111a, and wall sections 2111b, 2111c, 2111d. The plate section 2111a makes up almost all the extent of the table top 2111. The wall sections 2111b and 2111c are formed at both ends of the plate section 2111a to extend in the longitudinal direction.

The wall section 2111d is formed at the end of the plate section 2111a to extend in the table top width direction. The wall sections 2111b, 2111c and 2111d can hold a cushion 2113 (see FIG. 2) and the receiving coil 114 (see FIG. 1) and so on. As shown in FIG. 3, the wall section 2111d includes a handle 2114.

Detailed embodiments of the structure of the table top 2111 will now be explained.

Figure 4:
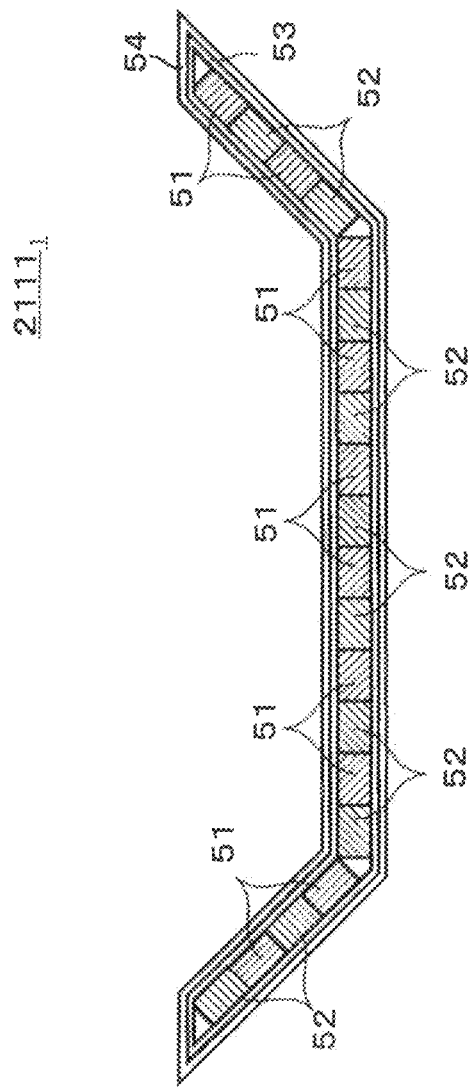
FIG. 4 is a cross-section showing a structure of a table top for an MRI apparatus according to an embodiment of the table top.

FIG. 4 is a cross-section showing a structure of a table top $2111_1$ according to an embodiment of the invention, along the width direction. Although FIG. 4 shows the outline of the relationship of the position of components of the table top $2111_1$, the sizes and measurements of each component can be varied.

As shown in FIG. 4, the table top $2111_1$ according to the embodiment includes a number of C-FRP molded material sections 51, a number of honeycomb material sections 52, a glass fiber layer 53, and an outer shell 54.

Figure 5:
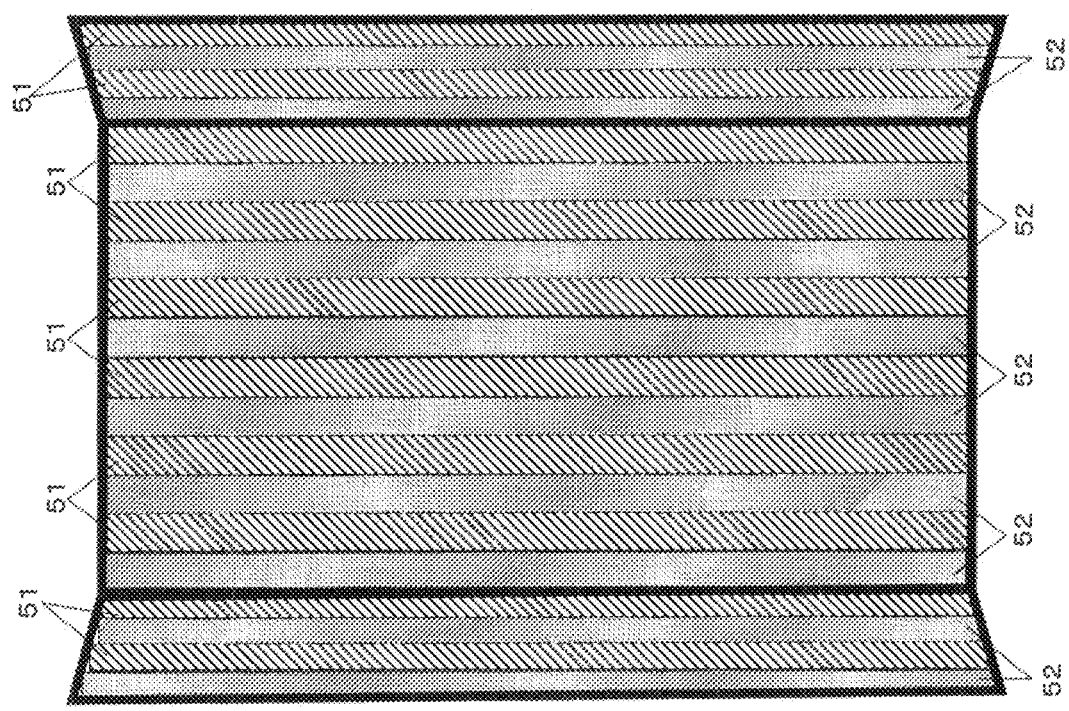
FIG. 5 is a plan view showing a structure of a table top for an MRI apparatus according to an embodiment of the table top.

FIG. 5 is an overhead plan view showing the structure of a table top $2111_1$ according to the embodiment.

As shown in FIG. 5, C-FRP molded material sections 51 are made of a longitudinal material of molded carbon fiber reinforced plastic that is long and narrow. The length of the longitudinal direction of the C-FRP molded material sections 51 is a little shorter than the total length of the table top longitudinal direction of the table top $2111_1$. The width of the C-FRP molded material sections 51 is sufficiently smaller than the length of the table top $2111_1$ in the width direction. A number of the C-FRP molded material sections 51 are placed so the longitudinal direction of them extends along the shape of the table top in the longitudinal direction. Thus, a number of C-FRP molded material sections 51 are placed parallel to each other.

The honeycomb material sections 52 are nonmagnetic and nonconductive, and are molded to be long and narrow and to have a honeycomb structure. For example, glass fiber reinforced plastic, paper, and resin are used as a material of the honeycomb material sections 52. Wood can be used as an insulation material that insulates a number of C-FRP molded material sections 51 instead of the honeycomb material sections 52. The length of the honeycomb material sections 52 are sufficiently smaller than the length of the table top $2111_1$ in the longitudinal direction. The width of the honeycomb material sections 52 is sufficiently smaller than the length of the table top 2111₁ in the width direction. As shown in FIG. 5, a number of honeycomb material sections 52 are placed in the plate section 2111a and the wall sections 2111b, 2111c shown in FIG. 3.

In addition, as shown in FIG. 4, the C-FRP molded material sections 51 and the honeycomb material sections 52 are placed in the plate section 2111a and the wall sections 2111b, 2111c of FIG. 3. The honeycomb material sections 52 are placed exposing a honeycomb shape of the honeycomb material 52 in the vertical direction of a plate of the table top 2111. Thus, the strength of the table top 2111 against a load coming from the vertical direction of the plate is increased.

The glass fiber layer 53 is formed of glass fiber in a cloth shape. As shown in FIG. 4, the glass fiber layer 53 is formed around the C-FRP molded material sections 51 and the honeycomb material sections 52, and keeps the C-FRP molded material sections 51 and the honeycomb material sections 52 in the plate state of the arrangement of FIG. 4. The glass fiber layer 53 can be formed one time around the C-FRP molded material sections 51 and the honeycomb material sections 52 or can be formed many times around the C-FRP molded material sections 51 and the honeycomb material sections 52.

The outer shell 54 is made from a nonmagnetic and nonconductive material, and covers the C-FRP molded material sections 51, the honeycomb material sections 52, and the glass fiber layer 53. Thus, a core structure of this embodiment is an arrangement in which a number of the C-FRP molded material sections 51 and a number of the honeycomb material sections 52 are alternately arranged in the table top 2111₁. The core structure prevents the table top 2111 from transforming or twisting about the table top longitudinal direction. However, because the strength of the C-FRP molded material sections 51 is higher than the strength of the honeycomb material sections 52, the prevention of the previous transformation depends mainly on the C-FRP molded material sections 51.

As shown in FIG. 4, a cross-section area of the C-FRP molded material sections 51 and a cross-section area of the honeycomb material sections 52 are nearly the same. Therefore, the ratio of the cross-section area of the C-FRP molded material sections 51 in the whole cross-section of the core is about ½. The strength of the C-FRP material depends on the filling ratio of carbon, and the strength of the C-FRP material is generally about 5 or 6 times higher than a G-FRP material. Therefore, the strength of the table top 2111₁ in the case that a number of C-FRP molded material sections 51 are partially placed in the table top 2111₁ can be increased greater than in the case of the table top being molded using the G-FRP. And because the specific gravity of C-FRP is lower than of G-FRP, and the specific gravity of the honeycomb material sections 52 is lower than G-FRP, when the table top 2111₁ is molded by using the honeycomb material sections 52 that have high air tightness, the table top 2111₁ can be made lightweight. Furthermore, the C-FRP molded sections 51 individually have a simple shape, and their cross-section area is small. Thus, the C-FRP molded material sections 51 are molded relatively easily with a simple processing.

In addition, the honeycomb material sections 52 do not have the strength of the C-FRP molded material sections 51, but still assist in prevention of transformation of the table top 2111₁. Furthermore, when the table top 2111₁ is shaped, a resin is poured into the inside of the glass fiber layer 53.

The honeycomb material sections 52 also have a function of a spacer to prevent too much resin from running into the inside of the glass fiber layer 53 and making the table top 2111₁ heavier than necessary.

Also, because the C-FRP material is conductive, an induced electric current generates a magnetic field, and the magnetic field could effect the observation of the magnetic resonance phenomenon. However, the honeycomb material sections 52 insulate the C-FRP molded material sections 51 from each other. Therefore, the C-FRP molded material sections 51 do not significantly affect the observation of the magnetic resonance phenomenon. A number of the C-FRP molded material sections 51 placed in the table top 2111₁ is variable while still maintaining the size of the table top 2111, for example by making the cross-section area of the C-FRP molded material sections 51 smaller and increasing the number of the C-FRP sections within the table top 2111. Because the smaller the cross-section area of the electrical conducting material the lower the induced current is, the induced current that is generated on each C-FRP molded material section 51 can be reduced. Therefore, the magnetic field that the induced current generates and any adverse effect of observation of the magnetic resonance phenomenon can be minimized.

In addition, as shown in FIG. 5, the C-FRP molded material sections 51 are placed so their longitudinal direction extends along the shape of the table top 2111₁ in the longitudinal direction, and the honeycomb material sections 52 are placed so their longitudinal direction also extends along the shape of the table top in the longitudinal direction, and they are placed between the C-FRP molded material sections 51. But such an arrangement of the C-FRP molded material sections 51 and the honeycomb material section 52 is non-limiting.

Figure 6:
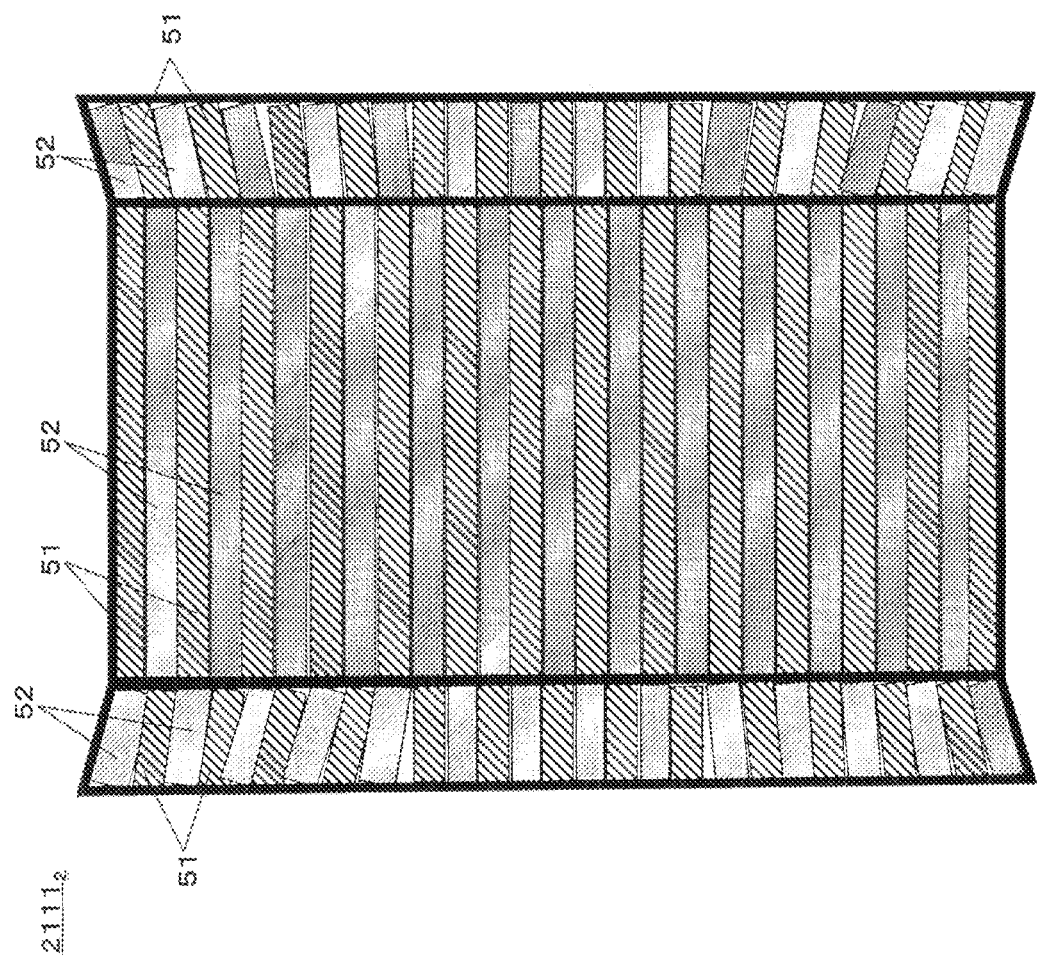
FIG. 6 is a plan view showing a structure of a table top for an MRI apparatus according to an embodiment of the table top.

For example, as shown in FIG. 6, showing a table top 2111₂ as a modification of the above-discussed embodiment, the C-FRP molded material sections 51 can be placed so their longitudinal direction extends along the shape of the table top 2111₂ in a width direction, and the honeycomb material sections 52 can be placed so their longitudinal direction extends along the shape of the C-FRP molded material sections 51 in the width direction.

Figure 7:
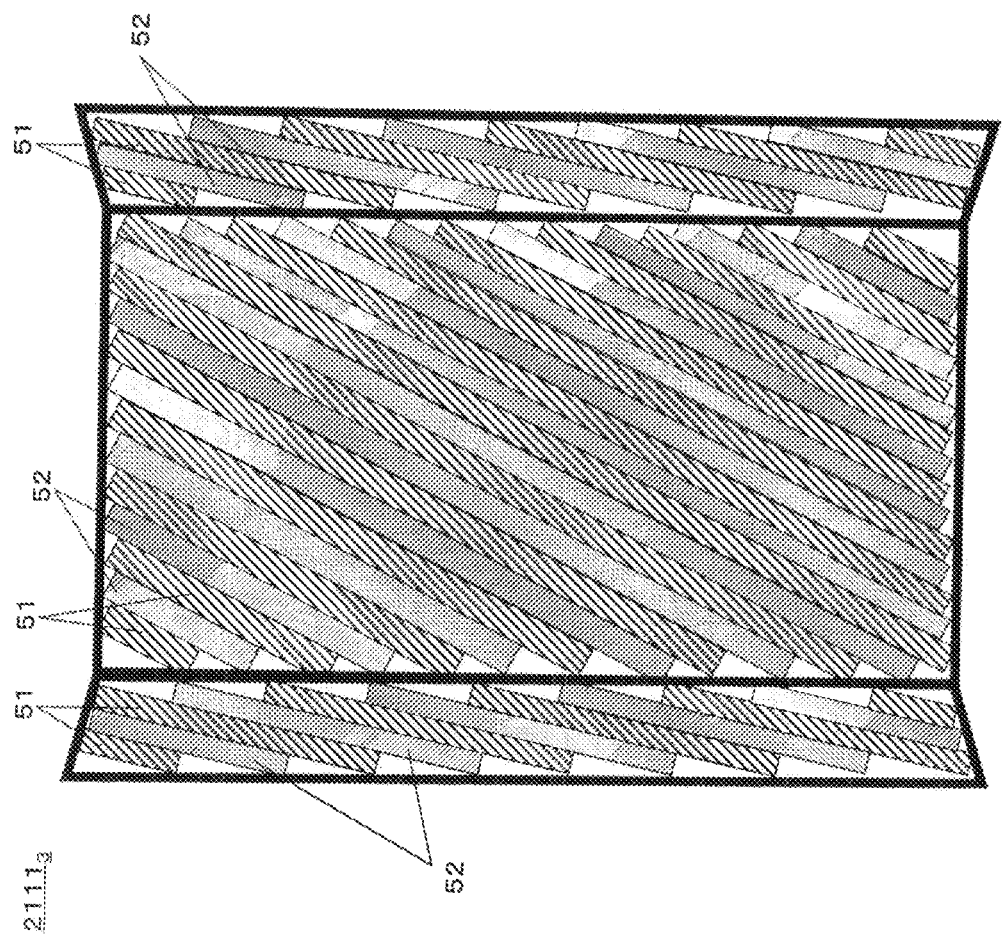
FIG. 7 is a plan view showing a structure of a table top for an MRI apparatus according to an embodiment of the table top.

As another example shown in FIG. 7 showing a table top 2111₃ as another modification of the above-discussed embodiment, the C-FRP molded material sections 51 can be placed so their longitudinal direction does not extend along the shape of the table top in the longitudinal or width direction, but instead at an angle to both the longitudinal and width directions, and the honeycomb material sections 52 can be placed so their longitudinal direction also does not extend along the shape of the table top in the longitudinal or width direction, but instead at an angle to both the longitudinal and width directions, and placed between the C-FRP molded material sections 51. In particular, the arrangement shown in FIG. 7 can increase the strength of the table top 2111₃ about the longitudinal direction.

Figure 8:
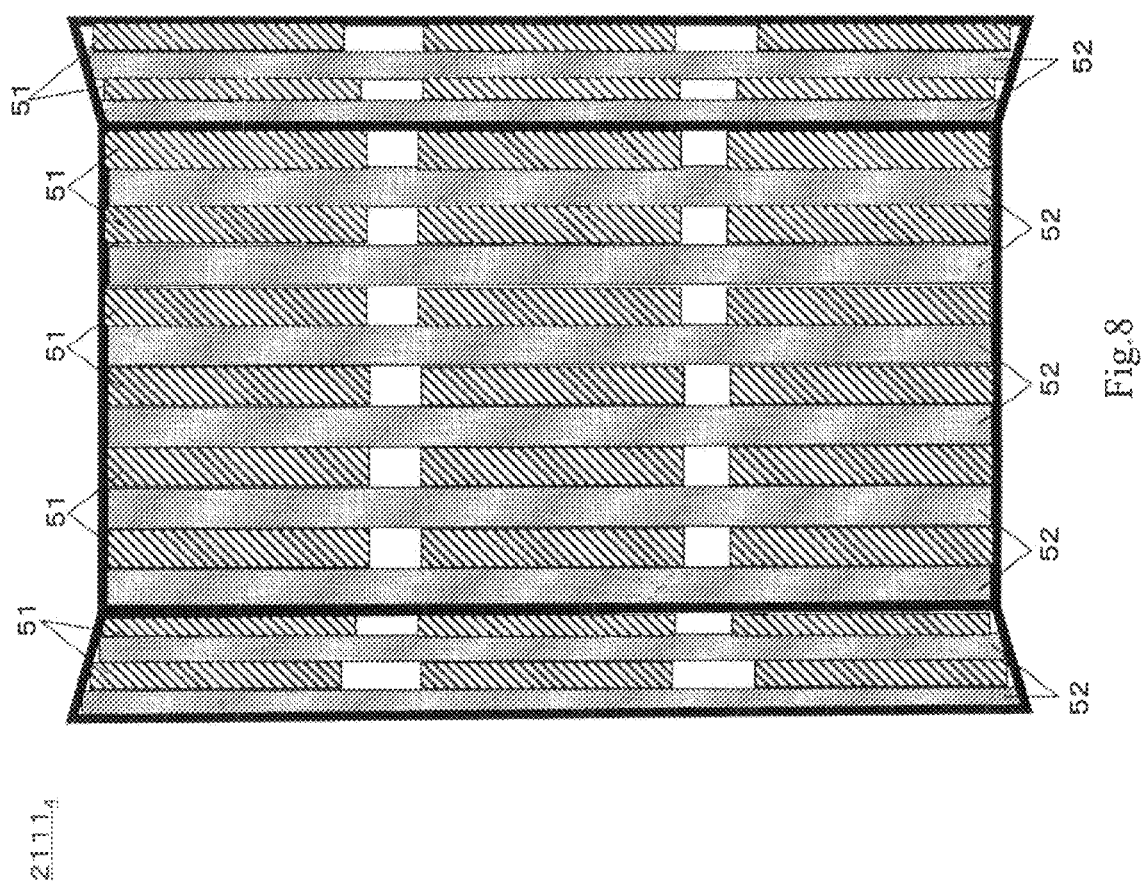
FIG. 8 is a plan view showing a structure of a table top for an MRI apparatus according to an embodiment of the table top.

Furthermore, the C-FRP molded material sections 51 on a table top 2111₄ according to another modification of the above discussed embodiment can be divided into plural separate areas, as shown in FIG. 8. The melting resin can be poured into the space between the C-FRP molded material sections 51 that are divided and the C-FRP molded material sections 51 can be insulated from each other by placing the honeycomb material sections 52 between the C-FRP molded material sections 51.

The divided C-FRP molded material sections 51 can be molded easier in this embodiment of FIG. 8 and the divided C-FRP molded material sections 51 can lighten the table top 2111 more than if the C-FRP molded material sections 51 are not divided.

Figure 9:
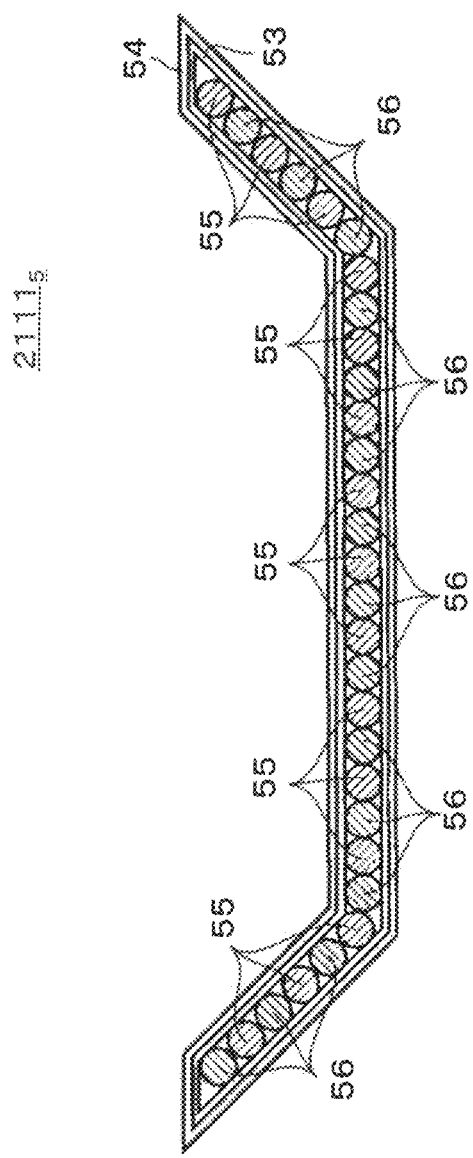
FIG. 9 is a cross section showing a structure of a table top for an MRI apparatus according to another embodiment of the table top.

FIG. 9 is a cross-section showing a structure of a table top 2111₅ according to another embodiment of the invention. And in FIG. 9, the same parts of the embodiment of FIG. 4 are indicated by the same reference indicators, and their explanation in detail will be skipped. However, FIG. 9 shows the outline of the relationship of the position of components of the table top 2111₅ of this embodiment, although the dimensions and spacing of each component can be varied in practice.

As shown in FIG. 9, the table top 2111₅ according to this embodiment includes the glass fiber layer 53, the outer shell 54, a number of C-FRP pultrusion productions 55, and a number of G-FRP material sections 56. That is to say, in this embodiment, the table top 2111₅ includes the C-FRP pultrusion productions 55 and the G-FRP material sections 56 instead of the C-FRP molded material sections 51 and the honeycomb material sections 52 of the embodiments of FIGS. 4-8.

The C-FRP pultrusion productions 55 are made of a longitudinal material molded to be long and narrow. The length of the C-FRP pultrusion productions 55 in the longitudinal direction is a little shorter than the length of the table top 2112 in the longitudinal direction, similar to the embodiment of FIGS. 4-8. The width of the C-FRP pultrusion productions 55 is sufficiently smaller than the length of the table top 2111₅ in the width direction. A number of the C-FRP pultrusion productions 55 are placed so their longitudinal direction extends along the shape of the table top longitudinal direction, and with a spacing between each other. Thus, a number of C-FRP pultrusion productions 55 are placed parallel to each other between the G-FRP material sections 56.

The G-FRP material sections 56 are of a longitudinal material molded to be long and narrow. The width of the G-FRP material sections 56 is sufficiently smaller than the length of the table top in the longitudinal direction. A number of the G-FRP material sections 56 are placed so their longitudinal direction extends along the shape of the table top in the longitudinal direction, and are placed between the C-FRP pultrusion productions 55.

The glass fiber layer 53 is formed around the C-FRP pultrusion productions 55 and the G-FRP material sections 56, and keeps the C-FRP pultrusion productions 55 and the G-FRP material sections 56 in the plate state of the arrangement of FIG. 9. The outer shell 54 covers the C-FRP pultrusion productions 55, the G-FRP material sections 56, and the glass fiber layer 53.

Thus, a core structure of this embodiment is an arrangement in which a number of the C-FRP pultrusion productions 55 and a number of the G-FRP material sections 56 are alternately arranged in the table top 2111₅. The core structure prevents the table top 2111₅ from transforming or twisting about the table top longitudinal direction. However, because the strength of the C-FRP pultrusion productions 55 is higher than the strength of the G-FRP material sections 56, the strength of the core according to this embodiment can be higher than a core formed by only the G-FRP material sections 56 in which the cross-section area is the same. And utilizing the C-FRP pultrusion productions 55 can provide sufficient strength by not requiring increasing the filling ratio of glass fiber. The G-FRP material sections 56 is not needed to provide high mechanical strength, and therefore it is not necessary to increase a ratio of the glass fiber. Furthermore, the C-FRP pultrusion productions 55 and the G-FRP material sections 56 individually have a simple shape, and the C-FRP pultrusion productions 55 and the G-FRP material sections 56 can be molded relatively easily with a simple processing.

The G-FRP material sections 56 are nonmagnetic and non-conductive. The G-FRP material sections 56 have a function that increase the strength of the core, and a function that insulates the C-FRP pultrusion productions 55 from each other. Because a number of the C-FRP pultrusion productions 55 are placed in the table top 2111₅, the cross-section area of the C-FRP pultrusion productions 55 can be made smaller regardless of the measurement of the table top 2111₅, compared with not including the C-FRP pultrusion productions 55. Because the C-FRP pultrusion productions 55 are insulated by the G-FRP material sections 56, the induced current that is generated on each C-FRP pultrusion productions 55 is low and the magnetic field that this induced current generates is low. Therefore, any adverse effects of observation of magnetic resonance phenomenon can be minimized.

In the above discussed embodiments, as shown for example in FIGS. 5 and 9, the C-FRP molded material sections 51 and the honeycomb material sections 52 or the C-FRP pultrusion productions 55 and the G-FRP material sections 56 of the table top 2111 are placed with their longitudinal direction extending in the longitudinal direction of the table top 2111, or as shown in FIG. 6 and FIG. 7, are placed with their longitudinal directions extending in a different direction than the longitudinal direction of the table top 2111. In fact, in the above-discussed embodiments, the C-FRP molded material sections 51 and the honeycomb material sections 52 or the C-FRP pultrusion productions 55 and the G-FRP material sections 56 are placed with their longitudinal directions being in the same direction to each other.

In a further embodiment, the arrangement of the C-FRP molded material sections 51 and the honeycomb material sections 52 or the C-FRP pultrusion productions 55 and the G-FRP material sections 56 is different from the arrangement in the above-discussed embodiments, as explained below.

Figure 10:
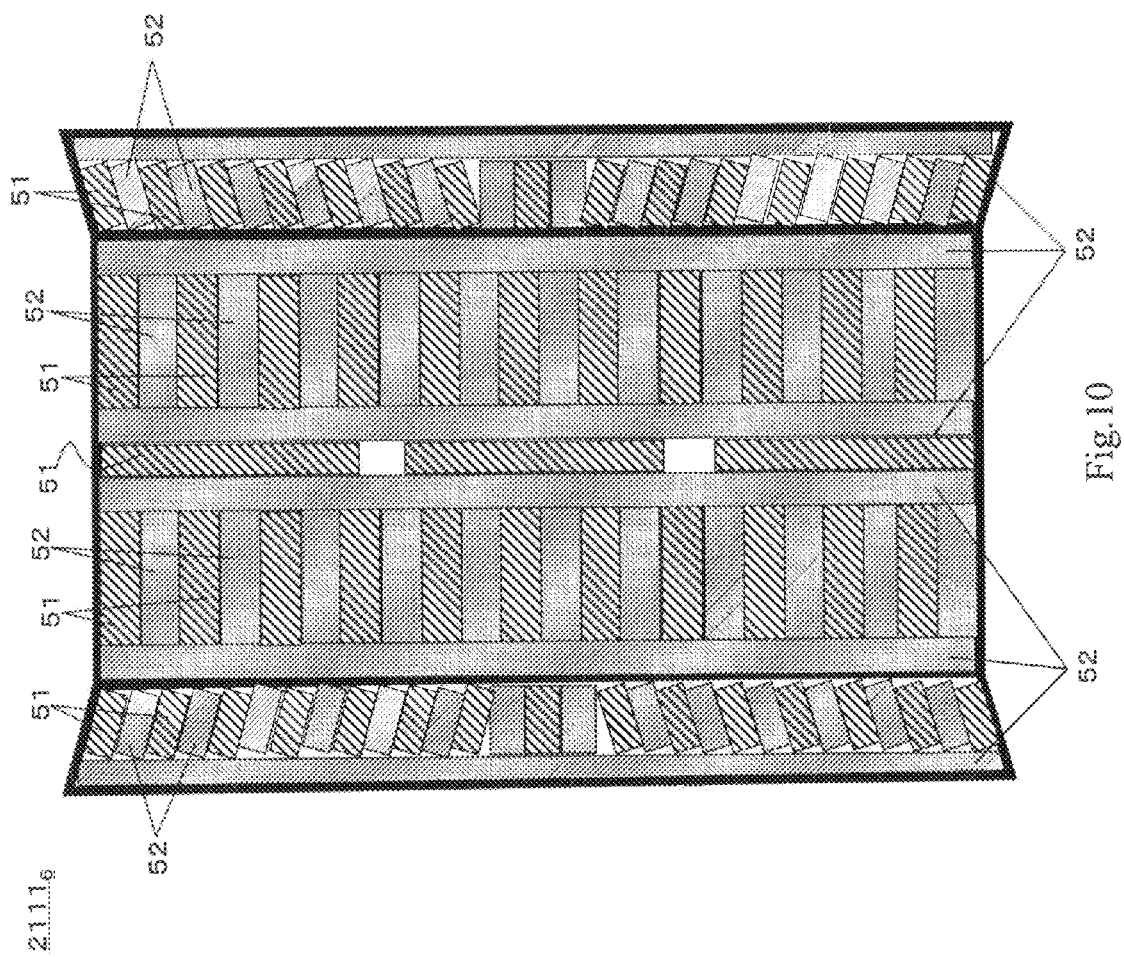
FIG. 10 is a plan view showing a structure of a table top for an MRI apparatus according to another embodiment of the table top.

FIG. 10 is an overhead plan view showing a structure of a table top 2111₆ according to another embodiment of the invention.

As shown in FIG. 10, in the table top 2111₆, some of the C-FRP molded material sections 51 are placed so their longitudinal direction extends along the shape of the longitudinal direction of the table top 2111₆, and with honeycomb material sections 52 between them, and some of the C-FRP molded material sections 51 are placed so their longitudinal direction extends along the shape of the table top 2111₆ in its width direction, with honeycomb material sections 52 between them.

Each C-FRP molded material section 51 is insulated from another C-FRP molded material section 51 by a honeycomb material section 52.

With this structure in FIG. 10, the load in every direction against the table top 2111₆ can be compensated for, and the strength of the table top 2111 can be increased. In addition, in this embodiment, as shown in FIG. 10, the C-FRP molded material sections 51 that are placed along the longitudinal direction of the table top 2111₆ are divided into several separate areas, and thereby the melting resin can be poured into the space between divided C-FRP molded material sections 51, and the honeycomb material sections 52 can be placed in the space between divided C-FRP molded material sections 51 to insulate C-FRP molded material sections 51 from each other. The C-FRP molded material sections 51 could alternatively be placed in the table top 2111₆ without dividing the C-FRP molded material sections 51.

Each of the above-discussed embodiments can be modified in various ways such as the following.

In the embodiment of FIGS. 4-8, a solid material can be used instead of the honeycomb material sections 52. However, because the honeycomb material sections 52 can maintain strength and provide a weight saving, it is preferred that the honeycomb material sections 52 are used.

Also in the embodiment of FIGS. 4-8, the cross-section shape of the C-FRP molded material sections 51 and the honeycomb material sections 52 can be various shapes, for example a circular or an oval figure, and the cross-section shape of the C-FRP molded material sections 51 can be different from the cross-section shape of the honeycomb material sections 52.

In the embodiment of FIG. 9, the cross-section shape of the C-FRP pultrusion productions 55 and the G-FRP material sections 56 can be various shapes, for example an oval figure or a square-shaped, and the cross-section shape of the C-FRP pultrusion productions 55 can be different from the cross-section shape of the G-FRP material sections 56.

In the embodiments of FIGS. 4-9, the C-FRP molded material sections 51 and the honeycomb material sections 52, or the C-FRP pultrusion productions 55 and the G-FRP molded material sections 56, can be molded with a sandwich structure plate material matching the shape of the plate sections 2111*a* and the wall section 2111*b*, 2111*c* and 2111*d*, and the outer shell can be formed by a glass fiber layer.

In the embodiments of FIGS. 4-9, the melting resin can be poured into a gap between the C-FRP molded material sections 51 or the C-FRP pultrusion productions 55 and the resin can be set for insulating about the C-FRP molded material sections 51 and the C-FRP pultrusion productions 55. That is to say, the number of the insulating material sections can be reduced and the resin can perform their insulating function. In the embodiments of FIGS. 4-9, the C-FRP molded material sections 51 or the C-FRP pultrusion productions 55 can also be placed in the thickness direction.

The outline of the table top 2111 can also be changed in shape. For example, the angle of gradient of the wall sections 2111*b*, 2111*c* can be changed. And part or all of the wall sections 2111*b*, 2111*c* and 2111*d* can be eliminated.

Additional advantages and modifications will readily occur to those skilled in the art. Therefore, the invention in its broader aspects is not limited to the specific details and representative embodiments shown and described herein. Accordingly, various modifications may be made without departing from the spirit or the general inventive concept as defined by the appended claims and their equivalents. For example, some component of all components that are shown in each embodiment can be omitted. Furthermore, components of the different embodiments can be combined.

The invention claimed is:

1. A magnetic resonance imaging apparatus comprising:
a static magnetic field generating section configured to generate a static magnetic field in an imaging space into which a subject is placed;
a gradient magnetic field generating section configured to generate a gradient magnetic field in the imaging space into which the subject is placed, which adds to the static magnetic field generated by the static magnetic field generating section;
a transmitting section configured to transmit a radio frequency pulse to the imaging space;
a receiving section configured to receive a magnetic resonance signal from the subject;
a calculating section configured to reconstruct an image based on the magnetic resonance signal from the receiving section;
a table top having a long side in a longitudinal direction and a short side in a cross-direction and configured to support the subject; and
a bed device configured to move the table top into the imaging space;
wherein the table top comprises:
a plurality of unitary quadrangular shaped conductive and elongated material sections placed a distance apart from each other;
a plurality of unitary quadrangular shaped insulating material sections that are nonmagnetic and provided between respective of the plurality of conductive and elongated material sections; and
a layer positioned entirely around the conductive and elongated material sections and the insulating material sections, configured to hold the conductive and elongated material sections and the insulating material sections into a plate sheet shape.

2. The magnetic resonance imaging apparatus according to claim 1,
wherein the conductive and elongated material sections are made from carbon fiber reinforced plastic (C-FRP).

3. The magnetic resonance imaging apparatus according to claim 2,
wherein the insulating material sections are made from a nonmagnetic and insulating material; and
the conductive and elongated material sections and insulating material sections are staggered parallel to each other.

4. The magnetic resonance imaging apparatus according to claim 3,
wherein a longitudinal direction of the conductive and elongated material sections is substantially parallel to a longitudinal direction of the table top or a cross-direction of the table top.

5. The magnetic resonance imaging apparatus according to claim 3,
wherein a longitudinal direction of the conductive and elongated material sections is not parallel to either a longitudinal direction of the table top or a cross-direction of the table top.

6. The magnetic resonance imaging apparatus according to claim 3,
wherein a first group of the conductive and elongated material sections are placed substantially parallel to a first direction; and
a second group of the conductive and elongated material sections are placed substantially parallel to a second direction different from the first direction.

7. The magnetic resonance imaging apparatus according to claim 6,
wherein the first direction is substantially parallel to the longitudinal direction of the table top; and
the second direction is substantially parallel to the cross-direction of the table top.

8. The magnetic resonance imaging apparatus according to claim 6,
wherein the first direction and the second direction are not parallel to the longitudinal direction of the table top and are not parallel to the cross-direction of the table top.

9. The magnetic resonance imaging apparatus according to claim 1,
wherein the insulating material sections are made from glass fiber reinforced plastic (G-RFP).

10. The magnetic resonance imaging apparatus according to claim 1, wherein the insulating material sections have a structure of a honeycomb.

11. The magnetic resonance imaging apparatus according to claim 10,
wherein the insulating material sections are placed so that the structure of the honeycomb extends in a vertical direction of the table top.

12. A bed device for a magnetic resonance imaging apparatus comprising:
a table top having a long side in a longitudinal direction and a short side in a cross-direction and configured to support the subject, comprising:
a plurality of unitary quadrangular shaped conductive and elongated material sections placed a distance apart from each other;
a plurality unitary quadrangular shaped of insulating material sections that are nonmagnetic and provided between respective of the plurality of conductive and elongated sections; and
a layer positioned entirely around the conductive and elongated material sections and the insulating material sections, configured to hold the conductive and elongated material sections and the insulating material sections into a plate sheet shape; and
a support section configured to support the table top.

13. A bed device for a magnetic resonance imaging apparatus according to claim 12,
wherein the elongated material sections are made from carbon fiber reinforced plastic (C-FRP).

14. A bed device for a magnetic resonance imaging apparatus according to claim 13,
wherein the insulating material sections are made from a nonmagnetic and insulating material; and
the conductive and elongated material sections and insulating material sections are staggered parallel to each other.

15. A bed device for a magnetic resonance imaging apparatus according to claim 14,
wherein a longitudinal direction of the conductive and elongated material sections are substantially parallel to a longitudinal direction of the table top or a cross-direction of the table top.

16. A bed device for a magnetic resonance imaging apparatus according to claim 14,
wherein a longitudinal direction of the conductive and elongated material sections is not parallel to either a longitudinal direction of the table top or a cross-direction of the table top.

17. A bed device for a magnetic resonance imaging apparatus according to claim 14,
wherein a first group of the conductive and elongated material sections are placed substantially parallel to a first direction; and
a second group of the conductive and elongated material sections are placed substantially parallel to a second direction different from the first direction.

18. A bed device for a magnetic resonance imaging apparatus according to claim 17,
wherein the first direction is substantially parallel to the longitudinal direction of the table top; and
the second direction is substantially parallel to the cross-direction of the table top.

19. A bed device for a magnetic resonance imaging apparatus according to claim 17,
wherein the first direction and the second direction are not parallel to the longitudinal direction of the table top and are not parallel to the cross-direction of the table top.

20. A bed device for a magnetic resonance imaging apparatus according to claim 12,
wherein the insulating material sections are made from carbon fiber reinforced plastic (G-FRP).

21. A bed device for a magnetic resonance imaging apparatus according to claim 12,
wherein the insulating material sections have a structure of a honeycomb.

22. A bed device for a magnetic resonance imaging apparatus according to claim 21,
wherein the insulating material sections are placed so that the structure of the honeycomb extends in a vertical direction of the table top.

23. A table top of a bed device for a magnetic resonance imaging apparatus having a long side in a longitudinal direction and a short side in a cross-direction and configured to support the subject, comprising:
a plurality of unitary quadrangular shaped conductive and elongated material sections configured to be placed a distance apart from each other;
a plurality of unitary quadrangular shaped insulating material sections that are nonmagnetic and provided between respective of the plurality of conductive and elongated material sections; and
a layer positioned entirely around the conductive and elongated material sections and the insulating material sections, configured to hold the conductive and elongated material sections and the insulating material sections into a plate sheet shape.

24. A table top of a bed device for a magnetic resonance imaging apparatus according to claim 23,
wherein the conductive and elongated material sections are made from carbon fiber reinforced plastic (C-FRP).

25. A table top of a bed device for a magnetic resonance imaging apparatus according to claim 24,
wherein the insulating material sections are made from a nonmagnetic and insulating material; and
the conductive and elongated material sections and insulated material sections are staggered parallel to each other.

26. A table top of a bed device for a magnetic resonance imaging apparatus according to claim 25,
wherein a longitudinal direction of the conductive and elongated material sections are substantially parallel to a longitudinal direction of the table top or a cross-direction of the table top.

27. A table top of a bed device for a magnetic resonance imaging apparatus according to claim 25,
wherein a longitudinal direction of the conductive and elongated material sections are not parallel to either a longitudinal direction of the table top or a cross-direction of the table top.

28. A table top of a bed device for a magnetic resonance imaging apparatus according to claim 25,
wherein a first group of the conductive and elongated material sections are placed substantially parallel to a first direction; and
a second group of the conductive and elongated material sections are placed substantially parallel to a second direction different from the first direction.

29. A table top of a bed device for a magnetic resonance imaging apparatus according to claim 28,
wherein the first direction is substantially parallel to the longitudinal direction of the table top; and
the second direction is substantially parallel to the cross-direction of the table top.

30. A table top of a bed device for a magnetic resonance imaging apparatus according to claim 28,
   wherein the first direction and the second direction are not parallel to the longitudinal direction of the table top and are not parallel to the cross-direction of the table top.

31. A table top of a bed device for a magnetic resonance imaging apparatus according to claim 23,
   wherein the insulating material sections are made from glass fiber reinforced plastic (G-FRP).

32. A table top of a bed device for a magnetic resonance imaging apparatus according to claim 23,
   wherein the insulating material sections have a structure of a honeycomb.

33. A table top of a bed device for a magnetic resonance imaging apparatus according to claim 32,
   wherein the insulating material sections are placed so that the structure of the honeycomb extends in a vertical direction of the table top.

34. A magnetic resonance imaging apparatus according to claim 1, wherein the plurality of conductive and elongated material sections and the plurality of insulating material sections have substantially same cross-sections and substantially same lengths.

35. A bed device according to claim 12, wherein the plurality of conductive and elongated material sections and the plurality of insulating material sections have substantially same cross-sections and substantially same lengths.

36. A table top of a bed device according to claim 23, wherein the plurality of conductive and elongated material sections and the plurality of insulating material sections have substantially same cross-sections and substantially same lengths.

* * * * *